United States Patent [19]

Grussmark

[11] Patent Number: 4,875,856

[45] Date of Patent: Oct. 24, 1989

[54] ORTHODONTIC APPLIANCE FOR CLOSING SPACES AND CORRECTING MALOCCLUSION

[76] Inventor: Stephen M. Grussmark, 2901 S. Bayshore Dr., Coconut Grove, Fla. 33133

[21] Appl. No.: 235,318

[22] Filed: Aug. 23, 1988

Related U.S. Application Data

[63] Continuation-in-part of Ser. No. 122,904, Nov. 19, 1987, abandoned.

[51] Int. Cl.$^4$ .................................................. A61C 7/00
[52] U.S. Cl. .................................................. 433/18
[58] Field of Search ........................... 433/22, 8, 18, 19

[56] References Cited

U.S. PATENT DOCUMENTS

| | | | |
|---|---|---|---|
| 1,638,006 | 8/1927 | Aderer | 433/19 |
| 2,086,656 | 7/1937 | Woodward | 433/18 |
| 2,531,222 | 11/1950 | Kesling | 433/6 |
| 3,091,856 | 6/1963 | Goldstein | 433/18 |
| 3,337,957 | 8/1967 | Reed | 433/18 |
| 3,474,779 | 10/1969 | Wall, Jr. | 433/18 |
| 3,803,715 | 4/1974 | Wallshein | 433/18 |
| 3,849,885 | 11/1974 | Robins | 433/6 |
| 3,997,970 | 12/1976 | Hodgson | 433/19 |
| 4,054,997 | 10/1977 | Wallshein | 433/18 |
| 4,224,021 | 9/1980 | Foxman | 433/2 |
| 4,253,828 | 3/1981 | Coles et al. | 433/6 |
| 4,413,978 | 11/1983 | Kurz | 433/6 |
| 4,504,229 | 3/1985 | Garito et al. | 433/215 |
| 4,676,745 | 6/1987 | Zurita | 433/6 |

OTHER PUBLICATIONS

Offerman, Richard E., "A Diastema–Closing Device", Journal of Clinical Orthodontics, Jun. 1984, vol. XVIII, No. 6.

American Journal of Orthodontics, Nov. 1984, ad for "Pro'3 s Adaptor".

*Primary Examiner*—Robert Peshock
*Attorney, Agent, or Firm*—Lloyd L. Zickert

[57] ABSTRACT

An orthodontic appliance for closing spaces between two adjacent teeth which includes a bar of elastomeric material or an elastic element and ligature wire means or an inelastic element for securing the bar in place over the labial or buccal or lingual faces of the teeth. The ligature wire means includes ligature wire secured to one or both ends of the bar for mounting and tensioning of the elastomeric bar on adjacent teeth. The appliance may also be configured to include a pair of spaced elastomeric bars and used to correct spot malocclusion problems.

23 Claims, 3 Drawing Sheets

ORTHODONTIC APPLIANCE FOR CLOSING SPACES AND CORRECTING MALOCCLUSION

DESCRIPTION

This application is a continuation-in-part application of my copending application Ser. No. 122,904, filed Nov. 19, 1987 and now abandoned.

This invention relates in general to an orthodontic appliance for closing a space between two adjacent teeth, and more particularly to an appliance that is fixed in position on the teeth by the orthodontist and which is used when needed during or following orthodontic treatment of a patient to quickly and efficiently close a space between two teeth on one arch, and further to an appliance for correcting spot malocclusions.

BACKGROUND OF THE INVENTION

Heretofore, other than the usual bracket and archwire systems, there have been many appliances developed for use in orthodontically treating patients and particularly for closing spaces between teeth. These appliances have generally been of the removable type and therefore demand patient cooperation in order to obtain the desired result. Some are such that they move gingivally where they can injure the gum tissues.

For example, the well known tooth-positioning appliance disclosed in U.S. Pat. No. 2,531,222, which constitutes a custom-made appliance made of resilient material and having sockets for teeth arranged in their ideal position and fitting between the upper and lower arches, will operate to close spaces between teeth and correct malocclusions but require the devoted commitment of a patient for its use. This tooth-positioning appliance is removable and usually provided to the patient with instructions to use it for one or more periods of time every day. Thus, its value is wholly dependent on patient cooperation, as it cannot produce results unless it is used. It is also geared for treating all of the teeth on both arches. Moreover, extensive preparation is required in order to make and place the appliance since it must be made pursuant to the taking of impressions and thereafter the expenditure of considerable laboratory time. This requires careful preplanning and results in a delay of several days before the appliance is provided to the patient. It is also a relatively expensive appliance. So, in addition to the time period needed for making the appliance and its cost, it also requires committed cooperation by the patient.

There have been a number of other appliances made which also can function to close spaces, but most have involved the need for laboratory work and for use on more than two adjacent teeth. The same disadvantages above noted are present. Further, most of these appliances have been designed to be removable, which requires patient cooperation.

Some orthodontists have relied on the use of elastics which must be placed by the patient. While elastics can serve to close a space, a big disadvantage is that they can move into the gum tissues and cause damage to the tissues. This same problem could be encountered if one were to use elastic thread. Additionally, they can be easily dislodged and lost, thereby completely defeating their intended use.

It is well known that during orthodontic treatment in many cases a need arises for closing the spaces between two adjacent teeth. Sometimes this is caused by a mere relapse where the teeth have separated subsequent to the use of the normal fixed bracket appliance and systems. Most commonly the problem arises between the upper two front teeth where a diastema opening is created. Thus, the problem of diastema closing is one that often arises during the treatment of a patient after the usual fixed wire and bracket appliances have been removed.

It has also been known to provide a diastema closing device in the form of attachments bonded to the lingual surfaces of the centrals and serving to anchor the ends of a spring member which provides a force for closing the diastema. Considerable time is necessary in order to bond the attachments to the teeth and to adjust the spring member to provide the desired closing force.

Treatment of a patient where teeth are maloccluded has customarily been handled by using fixed appliances on each arch and applying forces along the arches as well as between the arches with elastics to obtain proper occlusion. Removable appliances which depend on vital patient cooperation have also been used. In some cases difficulty has been experienced in certain areas along the arches to establish proper occlusion which has resulted in the necessity of extended treatment time to obtain the proper occlusion. This delays final treatment and discharge of a patient and even sometimes results in the inability to ever solve the problem.

Further, there have been times following removal of appliances that teeth relapse into former positions in a certain segment along the occlusal plane and which require only attention to that segment in order to correct the problem. This usually requires application of a number of appliances and/or elastics in order to solve the problem.

Heretofore, it has also been known to use elastics or elastic thread to correct spot malocclusion problems, it being understood that spot malocclusion refers to a minor malocclusion site such as existing between one tooth on one of the arches and a pair of opposed teeth on the other arch that are to occlude with the one tooth. Reliability is not high because elastics and elastic thread can be easily dislodged, thereby defeating their intended purpose.

SUMMARY OF THE INVENTION

The present invention overcomes the above referred to space difficulties in providing an appliance that can be quickly and easily put into use by the orthodontist at a relatively low cost whenever faced with the need to close a space between two aligned teeth. Particularly, as above noted, the problem occurs at the diastema with the upper two central teeth which always are the most noticeable when a person smiles. It is not always practical to use a laboratory made appliance. The present invention provides an appliance that may be kept in stock at a relatively low cost by the orthodontist and which can readily be mounted in place in a matter of a few minutes to obtain the desired result of closing that space between two teeth. In this respect, the appliance of the present invention, while optionally being available in suitable sizes, can easily and quickly be mounted on a patient's teeth and activated for the purpose of closing a space between two teeth.

The invention includes a bar of elastomeric material or suitable elastic element and ligature wire means or suitable inelastic element attached to the bar which can be easily handled by the orthodontist and which serves to allow the orthodontist to quickly and easily attach the appliance to adjacent teeth. When in place, it is considered to be a fixed appliance, rather than a removable appliance. The ligature wire means may consist of one or more strands of wire secured to opposite ends of the bar, or multiple strands secured to one end of the bar and a loop secured to the other end of the bar, or ligature wire secured in any number of ways to the bar which will facilitate the mounting of the bar onto the teeth. Orthodontists are well versed in the use of ligature wire, as it is commonly used in some manner for most techniques.

The elastomeric bar is usually disposed mesiodistally across the labial or buccal faces of those teeth that are desired to be moved toward each other. When placed under tension, it will cause a movement of the teeth toward each other until the gap or space originally existing therebetween is closed and the teeth then abut each other. It should be appreciated that the bar may be disposed over the lingual surfaces of the teeth to be treated if desired. When mounting the appliance, the orthodontist will not only activate the elastomeric bar to exert the closing force but also to maintain the closed position so that thereafter the teeth will be retained in that closed position as long as necessary. When manipulating the ligature wire during the mounting of the appliance, the wire ends are suitably twisted together and therefore permanently connected such that the appliance is not to be removed by the patient. It therefore stays in place continually until later removed or replaced by the orthodontist.

It has been found that the appliance of the present invention greatly facilitates the closing of a diastema space or other space between two teeth within a relatively short period of time and without subjecting the patient to undue discomfort, or the need for braces or brackets or retainers.

The use of the present invention does not require any mounting of attachments to individual teeth, and it will be appreciated that it only requires the quick and easy ligature tying of an elastomeric bar to adjacent and substantially aligned teeth so that the finally desired result of closing a space can be quickly and efficiently accomplished.

While the appliance of the invention is preferably used for closing a space between adjacent teeth, it can also be used as a Class I elastic between teeth along the same arch or between the upper and lower arches, as a Class II or Class III elastic or up and down or cross-elastic.

Another form of the present invention overcomes the malocclusion problems heretofore encountered in bringing into proper occlusion certain areas of the arches that have proved to be difficult to handle and also to provide a device for quickly and easily correcting spot occlusion problems caused by relapse.

This appliance of the present invention is a combination elastomeric and ligature wire unit which includes at least one and usually a pair of elastomeric sections or links interconnected by ligature wire links or strands. More specifically, the ends of the elastomeric links are interconnected by the ligature wire links where a continuous wire link is connected between one of the two adjacent ends of the links and free strands are connected to the other ends of the links which when applied to the arches can be twisted together. The continuous link would be hooked over or mounted on a bracket or like appliance on one tooth of one arch and the elastomeric links would extend between the arches and between the opposite sides of the one tooth and to the outer sides of two adjacent teeth of the other arch. The free strands would then be trained over the brackets or like appliances of the two teeth of the other arch and the ends twisted together in order to place the elastomeric links under tension to apply a force that would bring the tooth of the one arch into proper occlusion with the pair of teeth of the other arch.

It can be appreciated that the spacing between the ends of the elastomeric links can be adjusted in order to accommodate the various types of spacing needed for properly disposing the elastomeric links between the arches. Further, it can be appreciated that mounting of the appliance of the invention may be done very quickly and easily.

The appliance may take one of three forms, one of which would include a continuous ligature wire strand extending between two of the ends of the elastomeric links and a continuous wire strand extending between the other two ends of the elastomeric links and whereby mounting of the appliance on the teeth would be done by forming a twist in one or both of the ligature wire strands in order to adjust the positions of the elastomeric links and also to apply a suitable tension to move the teeth on which the appliance is mounted into proper occlusion.

Another form would include a continuous wire strand extending between one of the opposite ends of each of the elastomeric links and a free ligature strand connected to each of the other of the ends of the links and whereby mounting of the appliance would include optional twisting of the continuous strand in order to adjust the proper location of the elastomeric links and the twisting together of the other free wire strands in order to further provide the adjustable positioning of the elastomeric links and to induce a proper tension in the links that would move the teeth on which the appliance is mounted into proper occlusion.

Still another form would include a single elastomeric bar or link having a pair of ligature wires connected to and extending from each end. The ligature wires at one end would be longer than those at the other end. The short ligature wires would be used to connect to a single bracket on a tooth, while the long ligature wires would be used to respectively train over the brackets on the opposing teeth and then be tied together so that the single elastomeric bar would be disposed between the arches under tension and cause the teeth to move under the forces of the link so that the malocclusion would be corrected.

It is therefore an object of the present invention to provide a new and improved appliance for use in quickly and efficiently closing a space between two adjacent and substantially aligned teeth.

A further object of the invention is to provide an appliance for closing a space between adjacent teeth that is not to be removed by the patient, and which includes an elastic element and an inelastic element, and where the elastic element is such as to inhibit gingival movement that could damage the gum tissues.

Another object of the present invention is in the provision of a combination elastomer-ligature wire appliance for use in closing a space between two adjacent teeth and which can be simply and easily mounted by the orthodontist in a non-removable posture which thereby avoids the necessity to rely upon the cooperation of the patient for using the appliance as with known patient removable appliances.

Another object of the present invention is the provision of a combination elastomer-ligature wire appliance which can be quickly and easily mounted under tension onto adjacent teeth by the orthodontist for closing a space between the teeth and which can serve to effect the closing within a short period of time.

Still another object of the present invention is in providing a diastema closing appliance that is universally applicable to any patient and immediately mountable onto adjacent teeth when the need arises so as to function for closing the diastema.

A further object of the invention is to provide a new and improved diastema closing device that is simply and inexpensively constructed and which may be removed in a matter of seconds by the orthodontist once it has completed the closing action for which it is designed.

It is another object of the present invention to provide a new and improved appliance for establishing occlusion between a pair of teeth of one arch and a tooth of another arch to correct spot malocclusion problems.

A further object of the present invention is in the provision of a combination elastomeric and wire ligature appliance for correcting spot malocclusion problems between teeth of the upper and lower arches.

A still further object of the present invention is to provide an appliance that may be quickly and easily fitted and mounted on brackets or like appliances to solve minor malocclusion problems between the arches.

Other objects, features and advantages of the invention will be apparent from the following detailed disclosure, taken in conjunction with the accompanying sheets of drawings, wherein like reference numerals refer to like parts.

DESCRIPTION OF THE INVENTION

Figure 1:
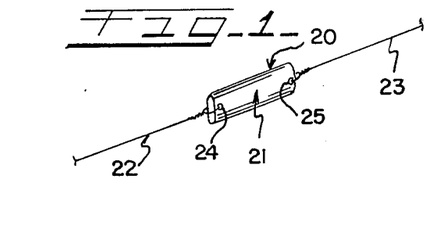
FIG. 1 is a perspective view of one embodiment of the diastema closing appliance of the invention.
Figure 2:
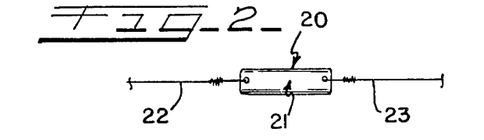
FIG. 2 is a front elevational view of the appliance of FIG. 1.
Figure 3:
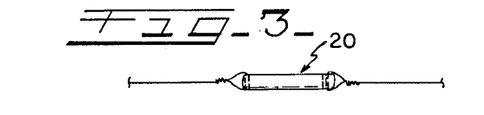
FIG. 3 is a top plan view of the appliance of FIG. 1.

Referring now to the drawings and particularly to FIG. 1, one embodiment of the orthodontic appliance of the invention is illustrated and generally indicated by the numeral 20. The appliance 20 includes an elastomeric bar 21 having a single strand of archwire 22 attached at one end of the bar and a single strand of ligature wire 23 attached to the other end of the bar. This appliance, when mounted onto adjacent substantially aligned teeth, functions as a space-closing appliance, as will be more clearly understood following the explanation of mounting the appliance. The bar 21 constitutes an elastic element, while the ligature wire constitutes an inelastic element.

The elastomeric bar 21 is made of a suitable elastomeric material having the capability of applying a force when under tension. Thus, it is elastic. It is also preferably formed to have some longitudinal stiffness such that when contacting the teeth will effect some rotational control during the closing action. There are many suitable synthetic materials available which are generally described as being of a plastic resin which, when stretched, will attempt to return to its original shape. The plastic material may be clear or of any suitable color. Preferably, it is of a material that will blend with the color of the teeth so as to be pleasingly acceptable to a patient. While the elastomeric bar may be of any suitable size, it is preferably on the order of two to four millimeters in vertical height and one to two millimeters in thickness. The length and shape may vary, depending upon the size of the teeth onto which it is to be mounted. For example, an acceptable length for most upper centrals will be five to ten millimeters long, but in any event the length would be such that when mounted on the adjacent teeth in a mesiodistal orientation, it would extend over approximately half of the mesiodistal width of each of the adjacent teeth at the location it is placed. It is important that it be sized to inhibit gingival movement into the gum tissues to preclude injury to these tissues. But it may take any form that will accomplish this purpose.

Figures 18, 19:
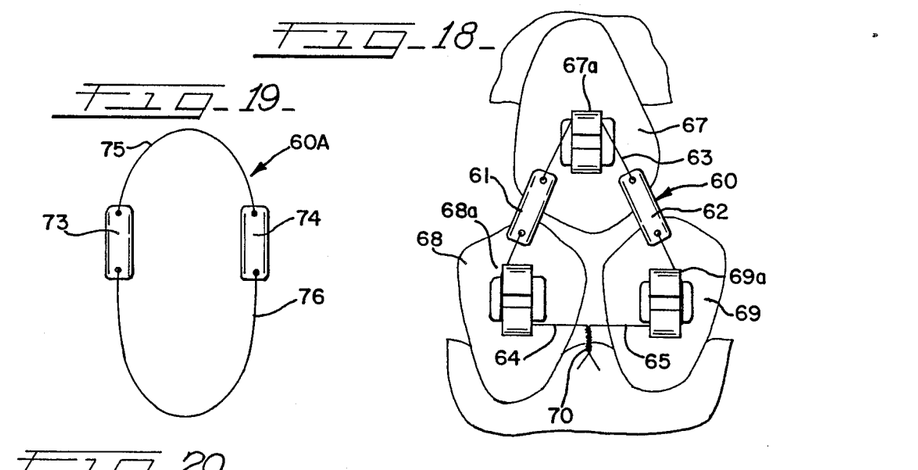
FIG. 18 is a labial or front elevational view of three teeth having appliances secured to the labial faces and including an appliance of the type in FIG. 17 mounted in place for the purpose of correcting a spot malocclusion problem observed between the three teeth.
FIG. 19 is a front elevational view of a modification of the appliance of FIG. 17 where continuous strands are interconnected between opposite ends of the elastomeric links.

The ligature wire strands 22 and 23 will be of the commercially available stainless steel ligature wire that is 0.006 to, 0.014 in diameter and which is essentially dead soft so that it can be easily manipulated when mounting the appliance on the teeth and therefore capable of being twisted together in tightly locked relationship. This wire is considered to be inelastic. While the strands may be connected to opposite ends of the bar in any suitable fashion, they are illustrated herein as being connected through holes formed in the bar. For example, ends of the strands may be molded into the bar or otherwise embedded in the bar. The strands 22 and 23 in FIG. 1 are respectively threaded through holes 24 and 25 formed at opposite ends of the bar 21 and then simply twisted on itself to complete the connection. The length of the ligature wire strands is preferably such that it can be easily manipulated during mounting of the appliance on the teeth and twisted together. The excess would be removed by a suitable wire-cutting pliers leaving only the twisted portions for locking the wire strands together. During the twist of the ends of the strands together, sufficient twisting is accomplished in order to place the elastomeric bar under a suitable tension so that it develops a force to close the space between adjacent teeth. It should be appreciated that a continuous strand could be attached at each end to the bar 21 in place of strands 22 and 23, whereby twisting a portion will tighten and tension the bar in place. An example of a continuous strand is shown in FIG. 19. While ligature wire is preferred, other flexible inelastic strands could be used.

Figure 4:
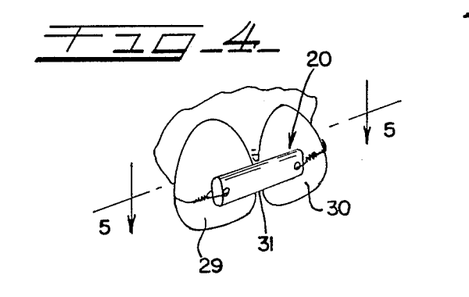
FIG. 4 is a perspective view of upper centrals having an appliance of the embodiment of FIG. 1 mounted in place.
Figure 5:
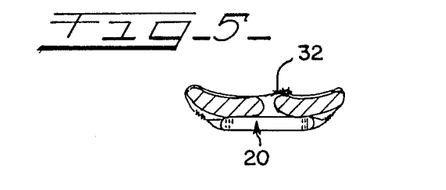
FIG. 5 is a cross-sectional view taken substantially along line 5—5 of FIG. 4 to illustrate the appliance in top plan view and mounted on the teeth.
Figure 6:
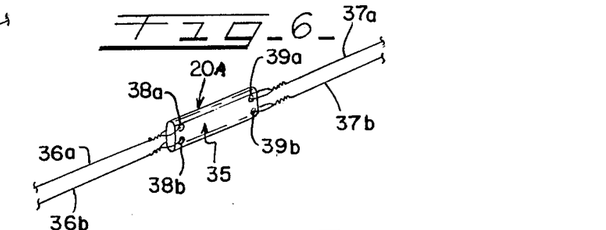
FIG. 6 is a perspective view of a modification which differs in that it includes a double strand of ligature wire at each end of the elastomeric bar.
Figure 7:
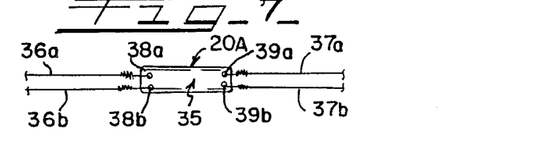
FIG. 7 is a front elevational view of the embodiment of FIG. 6.
Figure 8:
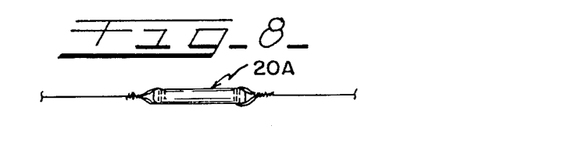
FIG. 8 is a top plan view of the embodiment of FIG. 6.
Figure 9:
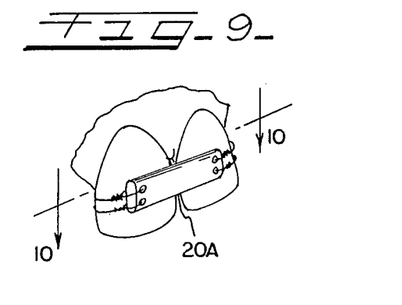
FIG. 9 is a perspective view of the embodiment of FIG. 6 in mounted relation on the upper centrals.
Figure 10:
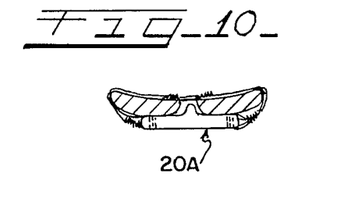
FIG. 10 is a sectional view taken substantially along line 10—10 of FIG. 9 and illustrating the appliance in top plan view as mounted on the centrals.
Figure 11:
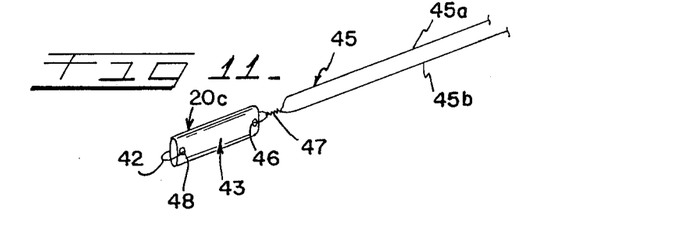
FIG. 11 is a perspective view of a still further modification of the invention which differs in that a loop of ligature wire or other material is mounted at one end of the elastomeric bar and a double stranded ligature wire is mounted at the other end of the bar.
Figure 12:
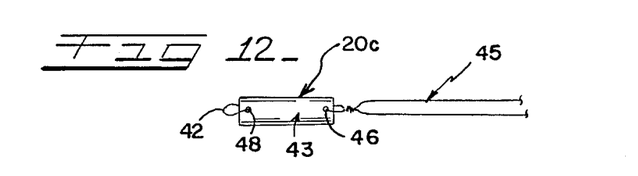
FIG. 12 is a front elevational view of the embodiment of FIG. 11.

Looking at FIG. 4, upper centrals 29 and 30 having a diastema space 31 existing therebetween are illustrated for receiving the appliance 20. The vertical position of the appliance is chosen by the orthodontist such that at least the engagement of the ligature wires at the distal edges of the centrals will be at or gingival of the widest point of the teeth so that the appliance will not have a tendency to be displaced occlusally. As seen in FIG. 5, the ends of the wires are twisted together at 32, the excess of the ligature wire strands already having been removed, and where the twisted ends may be bent to lie along one or the other of the strands.

Thus, to mount the appliance onto adjacent teeth, the orthodontist need only reach into his stock of appliances, choose an appropriate size if more than one is stocked, manually place the elastomeric bar over the labial or buccal or lingual surfaces of the teeth in a mesiodistal orientation, thread the opposed ligature wire strands distal to the teeth being brought together, join the strands together manually, and then with a suitable pliers twist the strands such as to place the elastomeric bar under tension. Thus, twisting of the strands together and placing the bar under tension activates the appliance. Thereafter, clipping off the excess of the ligature strands and bending the twisted tail to a suitable position completes the mounting of the appliance.

It has been found that anywhere between one and ten days the space 31 between the teeth will be closed by the appliance. Thereafter, the appliance will be removed and a suitable retainer or bonding may be used to stabilize the teeth. Alternatively, the appliance may be left in place a longer period of time and function as a retainer. Since the appliance is not to be removed by the patient, there is no need to rely on patient cooperation as required by patient removable appliances. Desired results therefore are obtained, as would be with any fixed appliance.

The size of the appliance is small compared to the teeth and therefore not objectionable to the patient. The resilient force set up by the appliance when it is activated is such that it will not be overly discomforting to the patient.

While not illustrated, it can be appreciated that the individual strands 22 and 23 of ligature wire could be a continuous strand extending from the opposite ends of the elastomeric bar 21 and then mounting of the appliance and activating it would merely require twisting together of the wire at one location to reduce the overall length and to tension the elastomeric bar and fix the position of the elastomeric bar on the teeth. This form of a wire ligature arrangement that interconnects both end is illustrated in another embodiment and particularly in FIG. 19 even though that embodiment includes a bar of elastomeric links.

Referring now to the embodiment of FIGS. 6 to 10, the modified appliance 20A is illustrated which differs from the closing appliance 20 only in that dual strands of ligature wire are connected to opposite ends of the elastomeric bar. This embodiment includes an elastomeric bar 35 having a pair of ligature wire strands 36a and 36b connected to one end and a pair of ligature wire strands 37a and 37b connected to the other end of the elastomeric bar. The strands 36a and 36b are connected by threading the strand through holes 38a and 38b and then twisting the wire on itself, while the strands 27a and 37b are similarly connected through holes 39a and 39b. So, the completed appliance includes the bar 35 of elastomeric material, with dual ligature wire strands 36a and 36b extending from one end and dual ligature wire strands 37a and 37b extending from the other end. This appliance would be mounted on a pair of substantially aligned and slightly spaced apart teeth in a similar manner as described for the mounting of appliance 20 on adjacent teeth, the difference being in that the dual strands at each end are trained over the distal edges of the teeth and then twisted together to lock the appliance in place under tension on the teeth. It may be appreciated that the strand 36a could be twisted together with the strand 37a or the strand 37b, while the strand 36b could be twisted together with either the strand 37a or 37b. Depending upon the contour of the teeth, it may be preferable to use the double-stranded ligature wire arrangement of this embodiment in order to provide the best possible mounting arrangement. Further, the use of dual strands increases the strength of the mounting arrangement and enables the use of a bar having a greater vertical dimension. So, this appliance would similarly be activated by being mounted under tension when the free ends of the ligature wire strands are twisted together. A greater force may be applied with this appliance inasmuch as the tensioning force of the elastomeric bar would be divided between the two strands. Nevertheless, the appliance 20A would function to close the space between two adjacent teeth.

Figure 13:
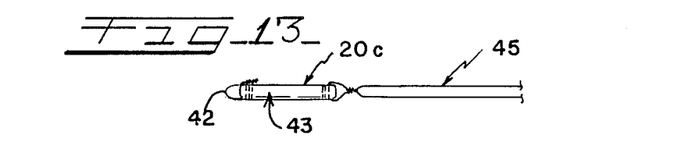
FIG. 13 is a top plan view of the embodiment of FIG. 11.
Figure 14:
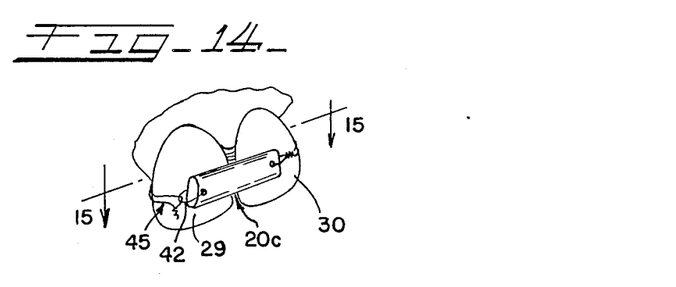
FIG. 14 is a perspective view of the appliance of FIG. 11 mounted to the upper centrals and the location of the twisted wire ends adjacent one end of the bar.

Another modification of the invention is illustrated in FIGS. 11 to 15, wherein the ligature wire means differs in that a loop 42 of wire or the like is secured to one end of the elastomeric bar 43, while a double-stranded ligature wire 45 having strands 45a and 45b is secured to the other end of the elastomeric bar. The double-stranded ligature wire is formed by a single strand of ligature wire threaded through a hole 46 in the one end of the elastomeric bar and twisted together at 47, leaving the opposite ends forming the double strands 45a and 45b. The loop 42 at the other end of the elastomeric bar is formed by a short strand of ligature wire threaded through a hole 48 and then twisted at the backside, as seen in FIG. 13. Both the wire 45 and loop 42 may be otherwise anchored in place such as during the molding of the bar. It may also be of other inelastic material than wire.

Figure 15:
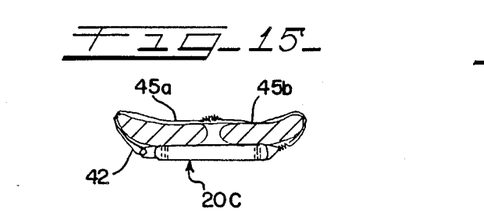
FIG. 15 is a sectional view taken substantially along line 15—15 of FIG. 14 and showing the embodiment of FIG. 11 in plan view as mounted on the upper centrals and the location of the twisted wire ends along the lingual.

When mounting the appliance 20C on the centrals 29 and 30, the elastomeric bar is disposed at the desired height along the teeth in a mesiodistal orientation. The free strands 45a and 45b are then trained over the adjacent distal edge of the tooth 30 back across the lingual surfaces of both teeth and over the distal edge of the tooth 29. One of the strands is then threaded through the loop 42 and then twisted together with the other strand until the elastomeric bar is placed under tension and activated. The excess wire is trimmed from the twisted portion and the twisted portion is then bent to a position where it will least likely be disturbed during occlusal action of the jaws. This embodiment is particularly useful where it is desired to eliminate the twisted tail or tails from being at the lingual side of the teeth, although the twisted tail may be disposed at the lingual as illustrated in FIG. 15. Once the embodiment is properly placed, it will function like the others in that it will apply a closing force to close the space between two teeth. It may further be appreciated that the loop 42 could be eliminated, and the wire 47 threaded through hole 48 and secured on itself.

Figure 16:
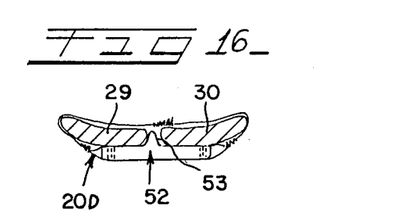
FIG. 16 is a view similar to FIG. 15 but showing a further modification of the invention wherein a safety lug is formed on the lingual side of the elastomeric bar to inhibit gingival and mesiodistal movement.

A further embodiment of the invention, designated 20D, is shown in FIG. 16 which differs from the embodiment in FIG. 1 only in that it includes an elastomeric bar 52 that is provided with a safety lug 53 on the lingual side which coacts with the space between the teeth on which the appliance is mounted to prevent gingival as well as mesiodistal movement of the elastomeric bar. This thereby assures that the bar remains in proper position mesiodistally on the teeth where it provides the best possible operation and provides safety from the appliance lodging below the gum tissues. The safety lug 53 is sized so that it will not interfere with the closing forces of the elastomeric bar, and it will not prevent the mesial edges of the teeth from closing toward one another and into abutting relation. It will be preferable to position the lug at the gingival of the bar where it will be aligned with the gap that normally exists between teeth that abut at the occlusal area. Otherwise, the appliance 20D will function in the same manner as the embodiment of FIG. 1.

While the appliance of the invention is illustrated as being used to close the diastema of the upper centrals, it should be appreciated that it may be used to close the gap or space between any two adjacent teeth. It will be apparent that when the appliance is used on teeth of smaller width than the upper centrals, the length of the elastomeric bar may be shortened so that when placed against the labial or buccal surfaces of the teeth, it will extend approximately over half the mesiodistal width of the teeth.

Figure 20:
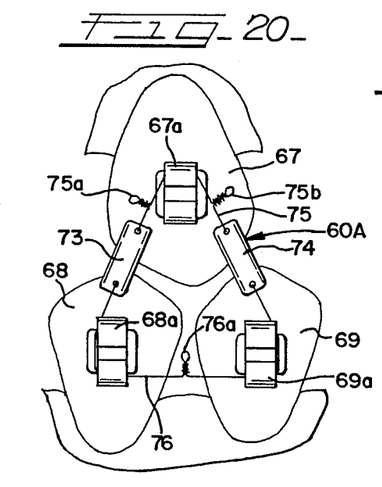
FIG. 20 is a view similar to FIG. 18 and illustrating the manner in which the modification of FIG. 19 is mounted on teeth of the upper and lower arches for developing suitable forces to correct a spot malocclusion problem.

It may further be appreciated that the appliance of the invention may be used as a Class I, Class II or Class III elastic along an arch or between arches whereby with reference to the embodiment of FIG. 20 one of the ligature wire strands may be secured to an attachment on one tooth, while the other ligature wire strand may be secured to an attachment on another tooth in a stretched condition so as to produce a force between the two teeth or groups of teeth.

From the foregoing, it may now be appreciated that this appliance of the present invention may be easily used by an orthodontist to close a space between two adjacent teeth in that it can be quickly and easily mounted and activated without the need of any special tools or custom laboratory work. Further, it can be appreciated that it is fixed in place on the teeth so that there is no need to rely on the cooperation of the patient.

Figure 17:
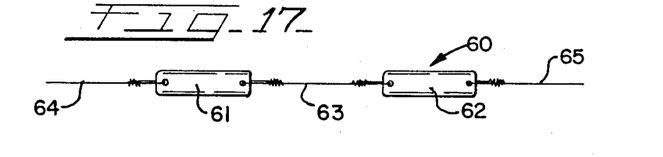
FIG. 17 is a front elevational view of a modified appliance according to the invention that includes a bar of elastomeric links interconnected by a strand of ligature wire and having at their free ends strands of ligature wire connected for mounting on appliances secured to the teeth.

Referring now to the embodiment of FIGS. 17 and 18, which illustrate the invention in a form for correcting spot malocclusions and particularly malocclusions that may exist between a single tooth of one arch and a pair of teeth of the opposite arch, an appliance generally designated by the numeral 60 includes a pair of elastomeric links 61 and 62 interconnected by a wire ligature strand 63 at adjacent ends and having freely extending wire ligature strands 64 and 65 extending from the other ends of the elastomeric links. It will be appreciated that the ligature wire strands may be connected to the elastomeric link in the same fashion as illustrated in the earlier embodiments or in any other suitable manner. Particularly, the wire ligature strands are connected to the end areas or portions of the elastomeric links. Use of this appliance 60 is particularly illustrated in FIG. 18 where it is mounted on tooth-mounted appliances of a pair of teeth in one of the arches and opposing teeth in the other arch. As illustrated, a single tooth 67 of the upper arch is in opposed relation to a pair of juxtaposed teeth 68 and 69 in the lower arch. It will be appreciated that here a malocclusion would be noted between teeth 67, 68 and 69 that could be easily corrected by applying forces between these teeth.

Mounting appliance 60 would, of course, require having a suitable bracket or like appliance already mounted on the labial surfaces of the teeth, as bracket 67a for tooth 67 and brackets 68a and 69a for teeth 68 and 69. The brackets illustrated are of the standard edgewise type, although it may be appreciated that ribbon arch brackets may be used or other types of appliances which would facilitate the anchoring of ligature wire. As illustrated, the interconnecting strand 63 is hooked over the gingival tie wing tips of the bracket 67a so that the elastomeric links 61 and 62 would extend or be disposed between the bracket 67a and the brackets 68a and 69a respectively. Wire ligature strand 64 would be trained over the tie wings of the brackets 68a, while wire ligature strand 65 would be trained over the tie wings of bracket 69a. The free ends of the wires would then be twisted together at 70 to form a suitable pigtail and then twisted to activate or tension the elastomeric links 61 and 62 so that a force is generated to draw the teeth 67, 68 and 69 into proper occlusion and then correct the malocclusion problem. The pigtail may be tucked back in between or near the interproximal of the teeth 68 and 69 in a usual manner.

If the length of the interconnecting strand 63 is too long, it may be shortened by twisting a portion of it together so that the desired position of the elastomeric links will be attained. It may also be appreciated that twisting a portion of strand 63 together could be the method of tensioning the elastomeric links 61 and 62.

Another form of double elastomeric link appliance is illustrated in FIGS. 19 and 20. The appliance by itself and in unmounted form is shown in FIG. 19 wherein the appliance is generally designated as 60A and includes a pair of elastomeric links 73 and 74 having their adjacent ends interconnected by ligature wire strands 75 and 76. Thus, the adjacent ends of links 73 and 74 on one end are connected by the wire ligature strand 75 and at the other end by the wire ligature strand 76. One of the strands may be made longer than the other and in this instance strand 76 is made longer than strand 75 inasmuch as it would be the strand intended to go over a pair of brackets. As seen in FIG. 20, the strand 75 is trained over the upper bracket 67a, while the strand 76 is trained over the lower brackets 68a and 69a. In order to adjust the positions of the elastomeric links, twists 75a and 75b may be made in the upper strand 75 to shorten it and twist 76a may be made in the lower strand 76 to shorten it. Further, it will be appreciated that any of the twists can be further twisted so as to define a tension condition for the links and for applying the necessary forces to overcome the malocclusion problem.

The appliance 60A may also be mounted in a manner other than described in the above paragraph, wherein following the hooking of strand 75 over the upper tie wing tip of bracket 67a, the strand 75 may be twisted together below the bracket prior to hooking strand 76 over brackets 68a and 69a. By twisting strand 75a, the length of the strand not only will be shortened, but it will also allow tensioning of the links 73 and 74 once the strand 76 is hooked over the lower brackets 68a and 69a.

Figures 21, 22:
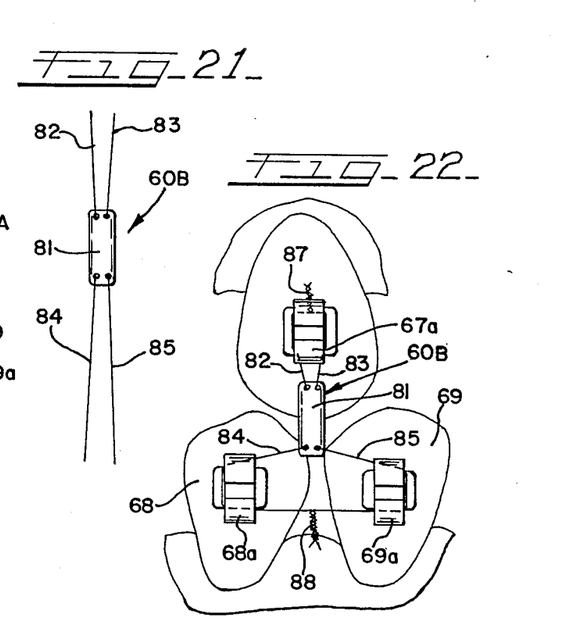
FIG. 21 is a front elevational view of a still further modified appliance for correcting spot malocclusion problems.
FIG. 22 is a view like FIG. 18 showing the appliance of FIG. 21 mounted in place and activated to correct a spot malocclusion problem.

Referring now to the embodiment of FIG. 21, the appliance, generally indicated by the numeral 60B, includes a single elastomeric link 81, a pair of short wire ligature strands 82 and 83 connected to one end of the link, and a pair of longer wire ligature strands 84 and 85 connected to the other end of the link. This appliance is mounted so that the elastomeric link 81 is disposed between the arches and is relatively centered between the lower teeth. The short wire strands 82 and 83 are trained over the upper bracket 67a and then twisted together at 87, while the longer wire ligature strands 84 and 85 are respectively trained over brackets 68a and 69a and then twisted together at 88. Tension would be applied to the elastomeric link 81 by either or both of the twists 87 and 88 to generate forces for bringing the respective teeth together into proper occlusion.

While the appliance 60B is shown in FIGS. 21 and 22 with a pair of individual wire strands extending from each end of the links 81, it may be appreciated that in place of the individual strands 82 and 83 a single continuous strand could be connected to the elastomeric link 81 whereby in mounting the appliance on the brackets a single continuous strand would merely be hooked over the upper bracket, after which the lower individual strands 84 and 85 would be hooked over the brackets 68A and 69A and then twisted together at their ends. It should also be understood that a single continuous strand could be substituted for the individual strands 84 and 85. Where the upper strands 82 and 83 are replaced by a single continuous strand, the pigtail needed and indicated at 87 for appliance 60B, as shown in FIG. 21, would be eliminated. In this instance, then, the continuous strand could be twisted together at the lower end of the bracket 67a to firmly secure the strand to the bracket.

It may now be appreciated that the appliances 60, 60A and 60B of the present invention may be quickly and easily mounted on appliances of the teeth to overcome a spot malocclusion problem and thereby avoid the need for any custom laboratory appliance or use of other appliances to correct such a spot malocclusion problem.

It may be further appreciated that one size may be used for all patients inasmuch as the free wire ends may be shortened by cutting to a desired size, and the distance or spacing between elastomeric links may be adjusted by twisting a portion to shorten the distance where desired.

It will be understood that modifications and variations may be effected without departing from the scope of the novel concepts of the present invention, but it is understood that this application is to be limited only by the scope of the appended claims.

The invention is hereby claimed as follows:

1. An orthodontic appliance for closing a space between two adjacent and substantially aligned teeth comprising, a bar of elastomeric material, and ligature wire means attached to said bar for securing the appliance to the teeth, said bar adapted to be disposed generally mesiodistally across the labial or buccal faces of the teeth and over the space therebetween, and said ligature wire means extending around the teeth and attached to opposite ends of said bar and being under tension to stretch said bar and produce a force to urge said teeth toward each other to close the space.

2. The appliance of claim 1, wherein said bar is of a length to at least extend across the space and over half the mesiodistal width of each tooth.

3. The appliance of claim 1, wherein the width of said bar is substantially twice the thickness.

4. The appliance of claim 1, wherein said ligature wire means includes a strand of ligature wire connected to at least one end of said bar.

5. The appliance of claim 1, wherein said ligature wire means includes a strand of ligature wire connected to each end of said bar.

6. The appliance of claim 1, wherein said ligature wire means includes a double strand of ligature wire connected to each end of said bar.

7. The appliance of claim 1, wherein said ligature wire means includes a double strand of ligature wire connected to at least one end of said bar.

8. The appliance of claim 1, wherein said ligature wire means includes a loop connected to one end of said bar and a pair of ligature wire strands connected to the other end of said bar.

9. The appliance of claim 1, wherein said bar further includes a centrally disposed lug extending lingually to engage between said teeth and inhibit gingival and mesiodistal sliding of said bar along the labial or buccal faces of the teeth.

10. The appliance of claim 1, wherein said bar is of a length to at least extend across the space and over half the mesiodistal width of each tooth, and said ligature wire means includes a strand of ligature wire connected to at least one end of said bar.

11. The appliance of claim 1, wherein said bar is of a length to at least extend across the space and over half the mesiodistal width of each tooth, and said ligature wire means includes a strand of ligature wire connected to each end of said bar.

12. The appliance of claim 1, wherein said bar is of a length to at least extend across the space and over half the mesiodistal width of each tooth, and said ligature wire means includes a double strand of wire connected to at least one end of said bar.

13. An orthodontic appliance for closing a space between two adjacent and substantially aligned teeth comprising, an elastic means, and an inelastic means attached to said elastic means for securing the appliance to the teeth, said elastic means adapted to be disposed generally mesiodistally across the labiobuccal or lingual faces of the teeth and over the space therebetween, and said inelastic means connected to opposite ends of said elastic means and extending around the teeth and being under tension to stretch said elastic means and produce a force to urge said teeth toward each other to close the space.

14. An orthodontic appliance for closing a space between two adjacent and aligned teeth of a patient, said appliance comprising, elastic means for applying a force to close the space to be disposed on the labiobuccal or lingual surfaces of the teeth, and inelastic means connected to said elastic means for attaching the appliance to the teeth so as not to be removed by the patient, said elastic means being of a length to extend mesiodistally over the space and at least about one-half of each of the labiobuccal or lingual surfaces of the teeth, and said inelastic means being connectible to the opposite ends of said elastic means and extending over the nonadjacent edges of the teeth and over the other of the labiobuccal or lingual faces of the teeth.

15. An orthodontic appliance for use as a Class I elastic to apply a force between teeth along the same arch or between the upper and lower arches, or as a Class II or Class III elastic or up and down or cross-elastic, which comprises a bar of elastomeric material, and a strand of ligature wire attached to each end of said bar for connecting the bar between two points under tension to stretch the bar and develop a pulling force to move teeth.

16. An orthodontic appliance for closing a space between two adjacent and substantially aligned teeth or for correcting spot malocclusion between opposing teeth which comprises an elastomeric bar having at least one wire ligature strand at each end, whereby mounting of the appliance to the teeth by the wire ligature strands such as to dispose and tension said bar between adjacent or opposed teeth applies such forces to close the space or correct the malocclusion.

17. An orthodontic appliance for correcting spot malocclusion between a tooth of one arch and a pair of teeth of the opposite arch which comprises, an elastomeric link having at least one wire ligature strand at each end, whereby mounting of the appliance to the teeth by the wire ligature strands such as to dispose and tension the elastomeric link between the arches applies such forces to the teeth to correct the spot malocclusion.

18. The appliance of claim 17, which includes a pair of wire ligature strands connected to each end of said link and the length of the strands at one end being greater than the length of the strands at the other end.

19. An orthodontic appliance for correcting spot malocclusion between a tooth of one arch and a pair of teeth of the opposite arch which comprises a pair of elastomeric links interconnected between their ends with wire ligature strands whereby mounting of the appliance disposes the elastomeric links between the arches to apply forces between the teeth on which the appliance is mounted to correct malocclusion.

20. An orthodontic appliance as defined in claim 19, wherein the ligature wire strand between one of the opposed ends of the elastomeric links includes free ends that may be twisted together when mounting the appliance on the arches.

21. An orthodontic appliance as defined in claim 19, wherein the strands between the links are continuous.

22. An orthodontic appliance as defined in claim 19, wherein one of the strands is continuous and the other is discontinuous.

23. An orthodontic appliance as defined in claim 19, wherein one of the strands is continuous and the other includes two segments having free ends.

* * * * *